US008128556B2

(12) United States Patent
Kimoto

(10) Patent No.: US 8,128,556 B2
(45) Date of Patent: Mar. 6, 2012

(54) BODY-INSERTABLE APPARATUS WITH POWER SUPPLY CONTROL

(75) Inventor: Seiichiro Kimoto, Akiruno-shi (JP)

(73) Assignee: Olympus Medical Systems Corp., Tokyo (JP)

(*) Notice: Subject to any disclaimer, the term of this patent is extended or adjusted under 35 U.S.C. 154(b) by 81 days.

(21) Appl. No.: 12/818,731

(22) Filed: Jun. 18, 2010

(65) Prior Publication Data

US 2011/0004066 A1 Jan. 6, 2011

Related U.S. Application Data

(63) Continuation of application No. PCT/JP2009/070696, filed on Dec. 10, 2009.

(30) Foreign Application Priority Data

Dec. 19, 2008 (JP) ................................ 2008-324137

(51) Int. Cl.
*A61B 1/06* (2006.01)

(52) U.S. Cl. ........ 600/118; 600/160; 600/178; 600/179; 320/117

(58) Field of Classification Search .................. 600/101, 600/109, 118, 160, 178, 179; 362/574; 320/117, 320/166
See application file for complete search history.

(56) References Cited

U.S. PATENT DOCUMENTS 6,368,270 B1 * 4/2002 Takami ........................ 600/178
6,595,756 B2 7/2003 Gray et al.
2004/0027459 A1 2/2004 Segawa et al.
2007/0171180 A1 * 7/2007 Akiyama ...................... 345/102
2007/0219435 A1 9/2007 Segawa et al.
2007/0260116 A1 * 11/2007 Shigemori et al. ............ 600/117
2008/0122291 A1 * 5/2008 Uchimoto et al. .............. 307/31
2008/0167528 A1 7/2008 Segawa et al.
2008/0180061 A1 * 7/2008 Koski et al. .................. 320/117
2008/0278970 A1 * 11/2008 Honda et al. ............... 363/21.01
2009/0099418 A1 * 4/2009 Kimoto ........................ 600/118
2009/0112058 A1 4/2009 Kagawa
2009/0187077 A1 * 7/2009 Hosoda et al. ................ 600/178

FOREIGN PATENT DOCUMENTS

JP 2001-224553 8/2001
JP 2004-065575 3/2004
JP 2005-000552 1/2005
JP 2005-152209 6/2005
JP 2005-245963 9/2005
WO WO 2008/001763 A1 1/2008

OTHER PUBLICATIONS

International Search Report dated Mar. 23, 2010.
Japanese Official Action dated Nov. 24, 2010 together with an English language translation.

* cited by examiner

*Primary Examiner* — John P Leubecker
(74) *Attorney, Agent, or Firm* — Scully, Scott, Murphy & Presser, P.C.

(57) ABSTRACT

A body-insertable apparatus includes: an illuminating unit that illuminates the inside of a subject's body; an imaging unit that takes an image of the inside of the subject's body; a first power supplying unit that supplies electric power to the imaging unit; a second power supplying unit that supplies electric power to the illuminating unit; and a switch that either connects the first power supplying unit to the second power supplying unit or disconnects the first power supplying unit from the second power supplying unit. The switch electrically separates the first power supplying unit from the second power supplying unit during at least an illuminating period of the illuminating unit.

6 Claims, 11 Drawing Sheets

10
POWER SUPPLY UNIT (BATTERY) :17
VCC
110: FIRST CIRCUIT
STORAGE UNIT
14
IMAGING UNIT
15
CONTROL UNIT
11
11a
TIMING CONTROL UNIT
12
13
SIGNAL PROCESSING UNIT
SENDING UNIT
SWITCH: SW18
120: SECOND CIRCUIT
121: ELECTRIC STORAGE UNIT
BOOSTER CIRCUIT
122
ILLUMINATING UNIT (LED) :16

ILLUMINATING UNIT (LED) :16
122
BOOSTER CIRCUIT
121A: POWER SUPPLY UNIT
120: SECOND CIRCUIT
IMAGING UNIT
15
TIMING CONTROL UNIT
13
SENDING UNIT
STORAGE UNIT
14
CONTROL UNIT
11a
12
11
SIGNAL PROCESSING UNIT
110: FIRST CIRCUIT
VCC
10A
POWER SUPPLY UNIT (BATTERY) :17

ILLUMINATING UNIT (LED) :16
122
BOOSTER CIRCUIT
POWER SUPPLY UNIT (BATTERY)
221: POWER SUPPLY (BATTERY)
220: SECOND CIRCUIT
SWITCH: SW18
IMAGING UNIT
STORAGE UNIT
TIMING CONTROL UNIT
CONTROL UNIT
11a
SENDING UNIT
SIGNAL PROCESSING UNIT
15
14
13
12
11
110: FIRST CIRCUIT
VCC
ELECTRIC STORAGE UNIT :217
20

OPERATION OF ILLUMINATING UNIT
OPERATION OF IMAGING UNIT
CONTROL SIGNAL Vcont
D1
ILLUMI-NATE
STORE CHARGE
READ IMAGE DATA
ILLUMI-NATE
STORE CHARGE
High
Low

BODY-INSERTABLE APPARATUS WITH POWER SUPPLY CONTROL

CROSS-REFERENCE TO RELATED APPLICATIONS

This application is a continuation of PCT international application Ser. No. PCT/JP2009/070696 filed on Dec. 10, 2009 which designates the United States, incorporated herein by reference.

BACKGROUND OF THE INVENTION

1. Field of the Invention

The present invention relates to a body-insertable apparatus and, more particularly, to a capsule body-insertable apparatus that is insertable into a subject's body and takes images of the inside of the subject's body.

2. Description of the Related Art

Capsule body-insertable apparatuses that include an imaging element (hereinafter, "capsule endoscope") have been developed. The capsule endoscopes are insertable into a subject's body via, for example, the oral route, take images of the inside of the subject's body, and wirelessly send the taken images (hereinafter, "in-vivo images") to an external device that is outside of the subject's body. An operator can observe the in-vivo images received by the external device and check subject's symptoms, etc., in order to perform a diagnosis.

SUMMARY OF THE INVENTION

A body-insertable apparatus according to an aspect of the present invention includes: an illuminating unit that illuminates the inside of a subject's body; an imaging unit that takes an image of the inside of the subject's body; a first power supplying unit that supplies electric power to the imaging unit; a second power supplying unit that supplies electric power to the illuminating unit; and a switch that either connects the first power supplying unit to the second power supplying unit or disconnects the first power supplying unit from the second power supplying unit, wherein the switch electrically separates the first power supplying unit from the second power supplying unit during at least an illuminating period of the illuminating unit.

A body-insertable apparatus according to another aspect of the present invention includes: illuminating means for illuminating the inside of a subject's body; imaging means for taking an image of the inside of the subject's body; first power supplying means for supplying electric power to the imaging means; second power supplying means for supplying electric power to the illuminating means; and switching means for either connecting the first power supplying means to the second power supplying means or disconnecting the first power supplying means from the second power supplying means, wherein the switching means electrically separates the first power supplying means from the second power supplying means during at least an illuminating period of the illuminating means.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
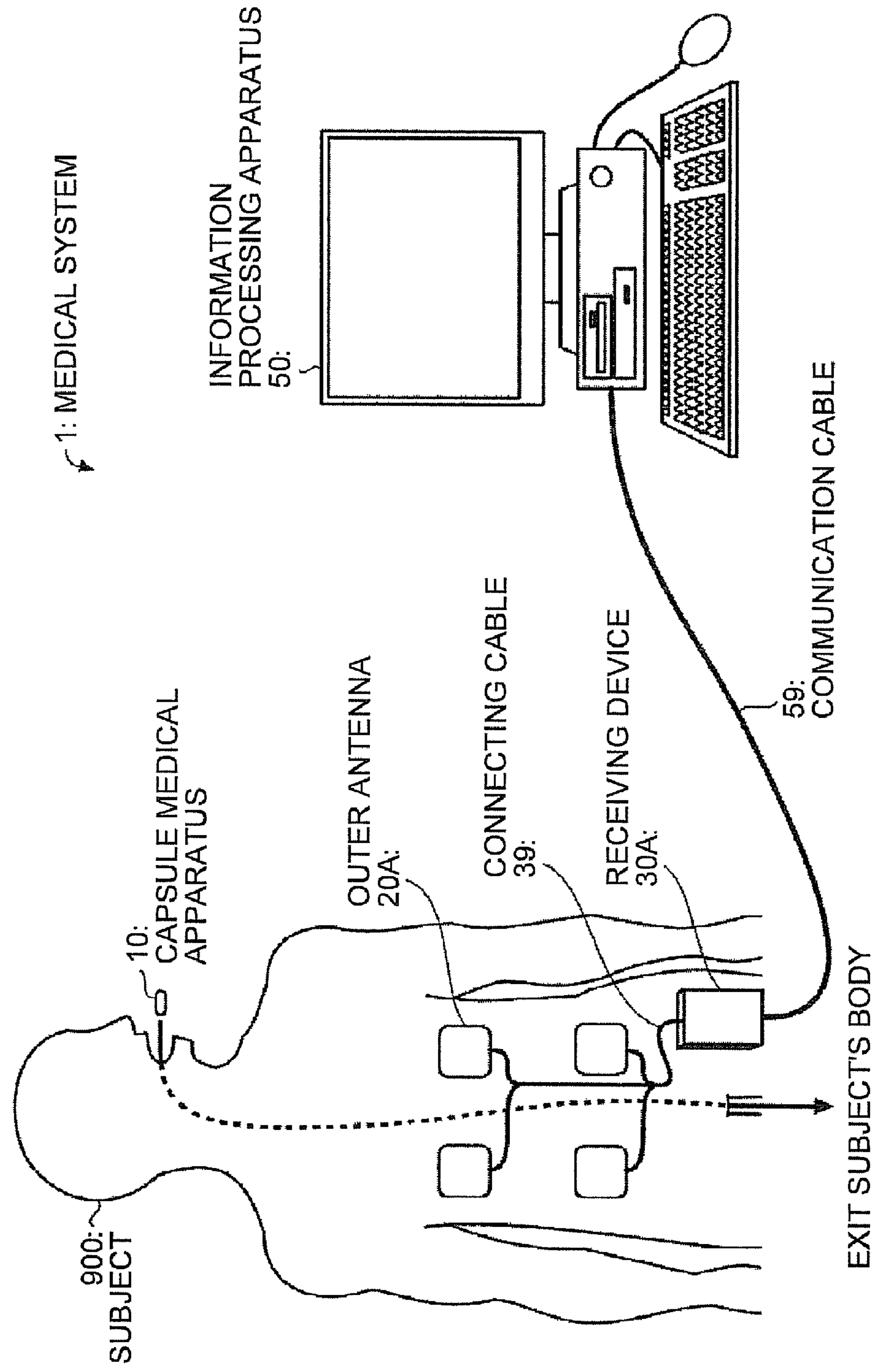
FIG. 1 is a schematic diagram of the configuration of a medical system according to any of a first, second, or third embodiment of the present invention.

Exemplary embodiments of the present invention are described in detail below with reference to the accompanying drawings. It should be noted that the present invention is not limited to the following embodiments. Moreover, the shape, the size, and the positional relation of the components described in the following are merely examples to make the contents of the present invention understandable and, therefore, the present invention is not limited to the shape, the size, and the positional relation of the components illustrated in the drawings. Furthermore, in some cross-sections of the drawings, some sections are not hatched for clarity. Moreover, the numerical values described in the following are merely examples and, therefore, the present invention is not limited to these numerical values.

First Embodiment

The configuration and operation of a medical system 1 according to a first embodiment of the present invention is described below with reference to the drawings. In the present embodiment, as an example of a body-insertable apparatus, a capsule medical apparatus 10 is used that is insertable into a subject 900 via the oral route and acquires information about the inside of the subject 900 (in-vivo information) while moving from the esophagus to the anus of the subject 900. It should be noted that the present invention is not limited thereto and some other capsule medical apparatuses can be used as a body-insertable apparatus of the present invention, for example, a medical device that acquires in-vivo information from the subject 900 while floating on liquid accommodated in organs, such as the stomach and the bowel. Moreover, as an example of the in-vivo information acquired by the capsule medical apparatus 10, images (in-vivo images) taken by a later-described imaging unit 15 are used in the present embodiment. However, the present invention is not limited thereto and some other types of information can be used, for example, the inner temperature, the inner pressure, the inner pH level of the subject.

FIG. 1 is a schematic diagram of the configuration of the medical system 1 according to the present embodiment. As shown in FIG. 1, the medical system 1 includes the capsule medical apparatus 10 small enough to be swallowed by the subject 900, a receiving device 30A that can receive image data containing the in-vivo images sent as wireless signals from the capsule medical apparatus 10, and an information processing apparatus 50 that can wirelessly or via a wire receive/send data from/to the receiving device 30A.

The receiving device 30A is connected to an outer antenna 20A via a connecting cable 39, a not shown balun (Balun), or similar. The wireless signal sent from the capsule medical apparatus 10 is received by the receiving device 30A via the outer antenna 20A.

The receiving device 30A is connected to the information processing apparatus 50 via, for example, a serial line or a parallel line. In the present embodiment, a USB interface is used to connect the receiving device 30A to the information processing apparatus 50 and the receiving device 30A is connected to the information processing apparatus 50 via a communication cable 59 that is a USB cable. It should be noted that the present invention is not limited thereto and the receiving device 30A can be connected to the information processing apparatus 50 in different connection methods, for example, via a card-type interface for a PC (Personal Computer) or the Bluetooth (registered trademark).

Moreover, the capsule medical apparatus 10 takes in-vivo images, for example, periodically and sends the image data to the receiving device 30A sequentially. Therefore, if the information processing apparatus 50 periodically repeats the process of receiving the image data from the receiving device 30A and displaying the image data thereon over and over, the information processing apparatus 50 can display substantially real-time in-vivo images for the user. If the image capturing cycle of the capsule medical apparatus 10 is set to, for example, two frames per second, the information processing apparatus 50 receives the image data from the receiving device 30A at least two times every second and displays the image data. This enables the substantially real-time in-vivo image display. The process in which the information processing apparatus 50 receives the image data from the receiving device 30A will be described in detail later.

Figure 2:
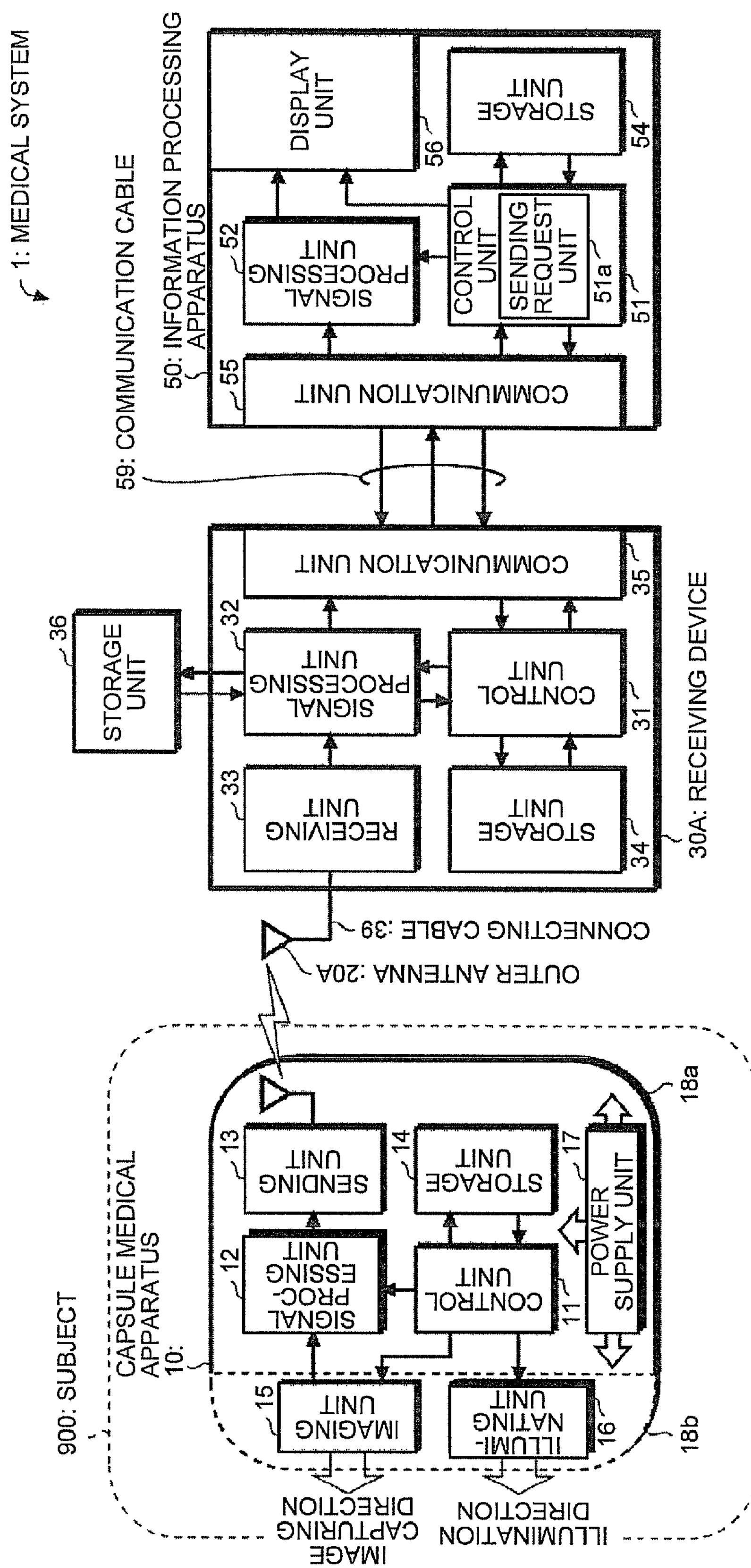
FIG. 2 is a block diagram of units making up the medical system according to any of the first, second, or third embodiments of the present invention.

The medical system 1 according to the present embodiment is described in detail below with reference to the block diagram of FIG. 2. FIG. 2 is a block diagram of units making up the medical system 1 according to the present embodiment.

As shown in FIG. 2, the capsule medical apparatus 10 insertable into the subject 900 includes, for example, the imaging unit 15 that takes images of the inside of the subject 900 and creates data signal containing the in-vivo images (hereinafter, "image data"); an illuminating unit 16 that illuminates the inside of the subject 900 when the imaging unit 15 takes the images; a signal processing unit 12 that processes the image data created by the imaging unit 15 in a predetermined manner; a sending unit 13 that sends the image data processed by the signal processing unit 12 to the receiving device 30A; a control unit 11 that controls the units of the capsule medical apparatus 10; a storage unit 14 that stores therein computer programs, setting data, etc., those necessary for the control unit 11 to control the units; and a power supply unit 17 that supplies a power to each unit of the capsule medical apparatus 10.

The control unit 11 operates the units of the capsule medical apparatus 10 in accordance with, for example, the computer programs and the setting data read from the storage unit 14, thereby causing the corresponding unit to, for example, take images or send data. The control unit 11 is, for example, a processor such as a CPU (Central Processing Unit) or an MPU (Micro Processing Unit).

The storage unit 14 stores therein the computer programs to be executed by the control unit 11 and parameters, etc., to be used with the computer programs. The storage unit 14 is, for example, a ROM (Read Only Memory). It should be noted that the storage unit 14 can include a RAM (Random Access Memory) on which the computer programs read by the control unit 11 are loaded.

Figure 3:
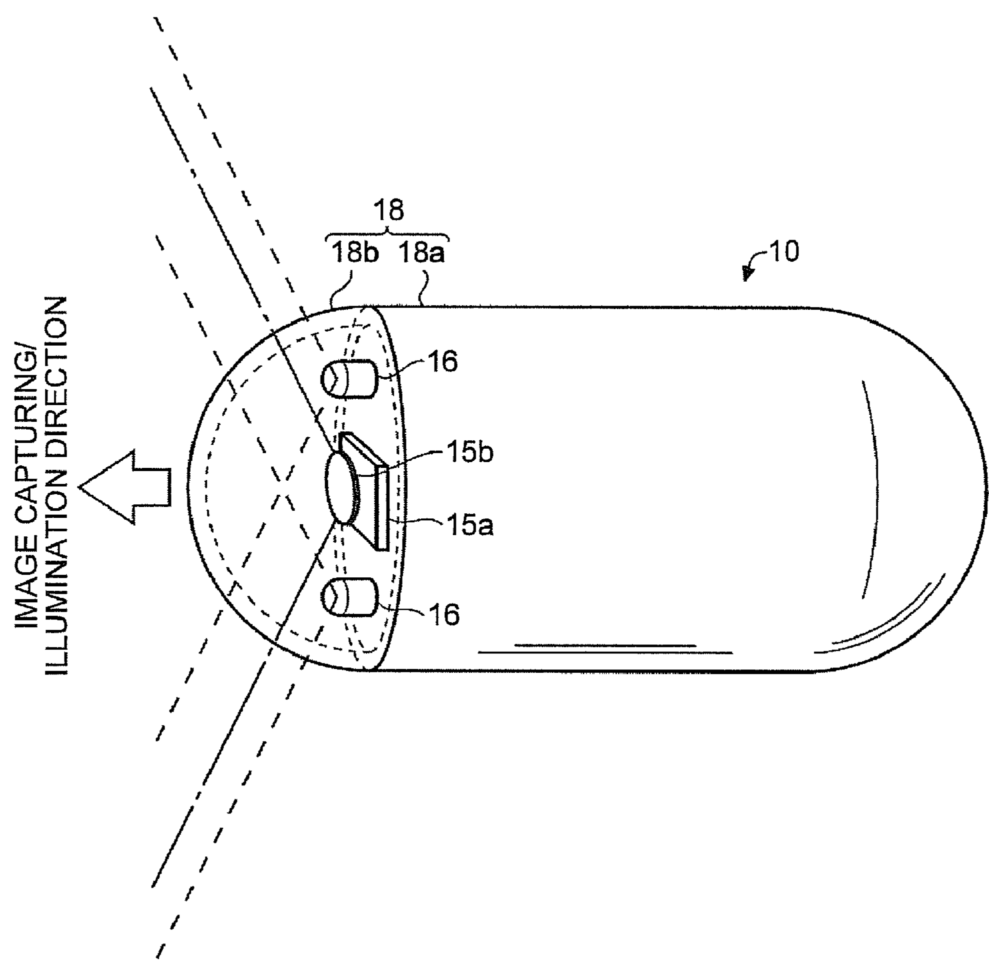
FIG. 3 is an outline view of a capsule medical apparatus according to any of the first, second, or third embodiments of the present invention.

As shown in FIG. 3, the imaging unit 15 includes, for example, a light-receiving element 15*a* that takes images of the inside of the subject 900 and creates the image data containing the images; an objective lens 15*b* that is at the light-receiving surface side of the light-receiving element 15*a*; and a driving circuit that drives these elements, being mounted on a not shown circuit board. On the circuit board, the illuminating unit 16 that illuminates the subject 900 with light for the image capture and its driving circuit are also mounted. The driving circuits of the imaging unit 15 and the illuminating unit 16 operate under the control of the control unit 11 so that the image data containing the in-vivo images are acquired, for example, periodically (e.g., two frames per second) and the image data is input to the signal processing unit 12. The operation of the capsule medical apparatus 10 during the image capture will be described in detail later. Moreover, in the following, it is assumed that each of the imaging unit 15 and the illuminating unit 16 includes its driving circuit. Moreover, the imaging unit 15 and the illuminating unit 16 in the present embodiment work as an in-vivo information acquiring unit that acquires the in-vivo information.

The signal processing unit 12 processes in a predetermined manner, under the control of the control unit 11, the analog image data received from the imaging unit 15, for example, performs sampling, amplification, and A/D (Analog to Digital) conversion, thereby creating digital image data. The processed image data is input to the sending unit 13.

The sending unit 13 processes, under the control of the control unit 11, the image data received from the signal processing unit 12, for example, superimposes the image data onto a reference frequency signal to be sent and performs modulations and up-conversion and then sends the processed image data as a wireless signal out of the capsule medical apparatus 10.

As shown in FIGS. 2 and 3, the units of the capsule medical apparatus 10 is accommodated in, for example, a capsule casing 18. The casing 18 includes, as shown in FIG. 3, a container 18*a* and a cap 18*b*, the container 18*a* having one end being hemispherical or dome shaped and the other end being substantially cylindrical shaped with an aperture, the cap 18*b* being fittable into the aperture of the container 18*a* for sealing the casing 18. The casing 18 is, for example, small enough to be swallowed by the subject 900. Moreover, in the present embodiment, at least the cap 18*b* is made of a transparent material. The circuit board on which the imaging unit 15 and the illuminating unit 16 are mounted is inside the casing 18 and is closer to the cap 18*b*. The element supporting surface of each circuit board faces toward the cap 18*b*. Therefore, as shown in FIGS. 2 and 3, the image capturing/illumination direction of the imaging unit 15 and the illuminating unit 16 is the direction toward the outside of the capsule medical apparatus 10 through the transparent cap 18*b*.

Although, in the present embodiment, the capsule medical apparatus 10 has one imaging unit 15, the present invention is not limited thereto and a plurality of imaging units and/or a plurality of illuminating units can be used in such a manner that, for example, the container 18*a* is a cylindrical shape with apertures on both ends, the transparent cap 18*b* is fit into the aperture on each end, and both the imaging unit 15 and the illuminating unit 16 are arranged at each side.

Moreover, the receiving device 30A in the present embodiment is on the outside of the subject 900 (e.g., the outer surface of the subject 900 or the clothes of the subject 900). The receiving device 30A includes, as shown in FIG. 2, a receiving unit 33 that receives the image data from the capsule medical apparatus 10; a signal processing unit 32 that processes the received image data in a predetermined manner; a control unit 31 that controls the units of the receiving device 30A; a storage unit 34 that stores therein computer programs, setting data, etc., those necessary for the control unit 31 to control the units; and a communication unit 35 that functions as an interface to communicate with the later-described information processing apparatus 50.

The control unit 31 operates the units of the receiving device 30A in accordance with, for example, the computer programs and the setting data read from the storage unit 34, thereby causing the corresponding unit to, for example, send the image data that has been received from the capsule medical apparatus 10 to the information processing apparatus 50. The control unit 31 is, for example, a processor such as a CPU or an MPU.

The storage unit 34 stores therein the computer programs to be executed by the control unit 11 and parameters, etc., to be used with the computer programs. The storage unit 34 is, for example, a ROM and/or a RAM. The storage unit 34 can be used as an execution area during when the control unit 31 executes the computer programs.

The receiving unit 33 processes, under the control of the control unit 31, the signal received from the capsule medical apparatus 10 via the outer antenna 20A, for example, performs filtering, down-conversion, demodulation, and decode, and then inputs the processed signal to the signal processing unit 32.

Under the control of the control unit 31, the signal processing unit 32 separates the image data from the data signal received from the receiving unit 33, reconfigures the image data, and inputs the reconfigured image data to the communication unit 35. After separating and reconfiguring the image data under the control of the control unit 31, the signal processing unit 32 can store the reconfigured image data in a portable storage unit 36 that is attachable to the receiving device 30A.

The communication unit 35 makes, under the control of the control unit 31, communications with a communication unit 55 of the information processing apparatus 50, thereby sending/receiving data to/from the information processing apparatus 50, the image data and data signals including request signals and response signals. The communication unit 35 is, for example, a USB interface or similar, and is connected to the above-mentioned communication cable 59. The communication unit 35 receives a USB bus power via, for example, the communication cable 59. The units of the receiving device 30A operate by using the USB bus power as the power source. However, the configuration is not limited thereto and the receiving device 30A can include an internal power source and the units of the receiving device 30A operate by the electric power received from the internal power source.

The configuration of the information processing apparatus 50 according to the present embodiment is described below in detail with reference to FIG. 2. The information processing apparatus 50 according to the present embodiment is, for example, an information processing apparatus, such as a personal computer having a computing function and a display function. As shown in FIG. 2, the information processing apparatus 50 includes the communication unit 55 that is an interface for communications with the receiving device 30A; a signal processing unit 52 that processes in a predetermined manner the image data received via the communication unit 55 and generates an image signal for displaying the image data; a display unit 56 that displays the in-vivo images in accordance with the image signal received from the signal processing unit 52; a control unit 51 that controls the units of the information processing apparatus 50 and performs calculations, etc.; and a storage unit 54 that stores therein computer programs that describe processes to be performed by the control unit 51 and setting data. The information processing apparatus 50, for example, receives the in-vivo images from the capsule medical apparatus 10 via the receiving device 30A and then displays the substantially real-time in-vivo images on the display unit 56.

Figure 4:
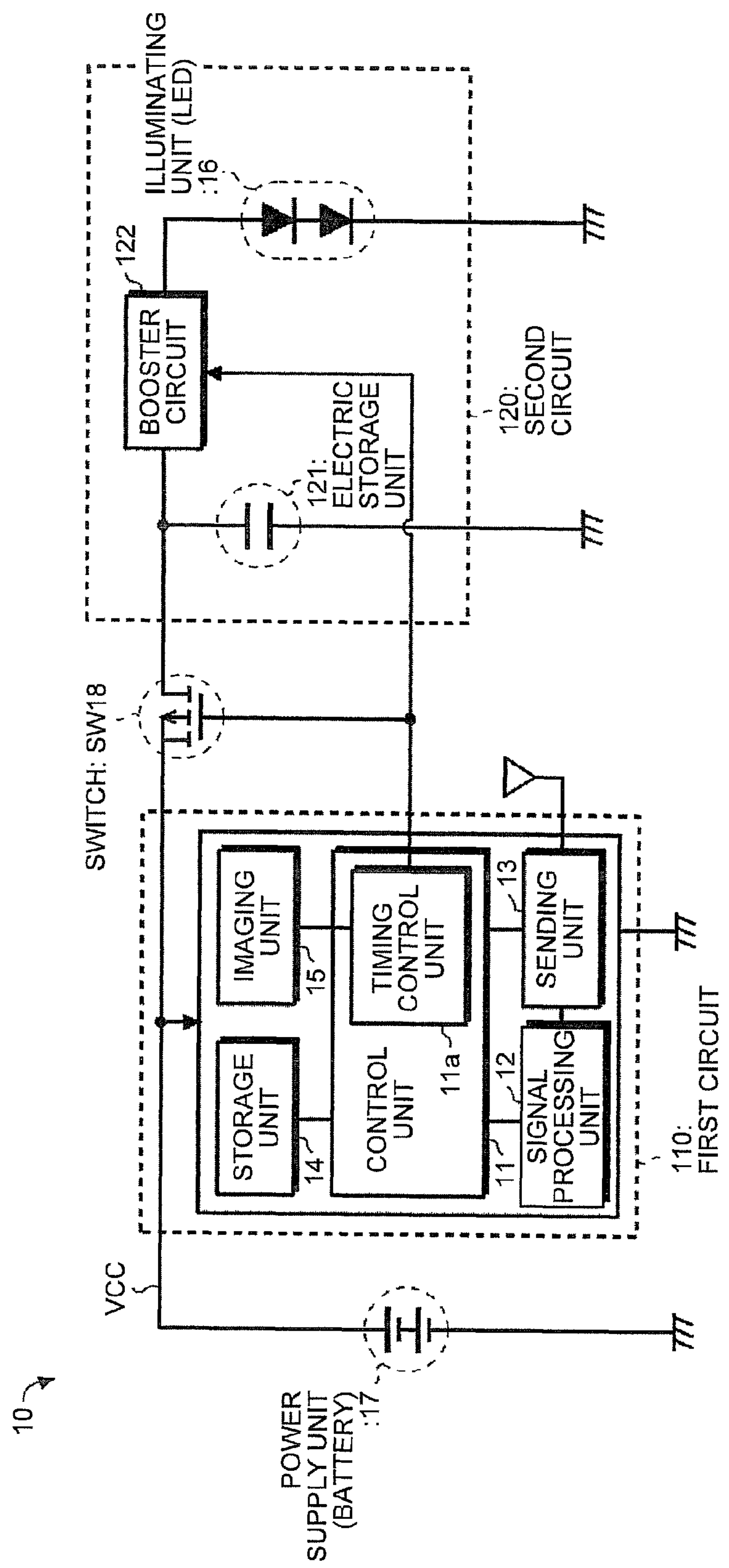
FIG. 4 is a block diagram of the configuration of the capsule medical apparatus according to the first embodiment of the present invention.

The operation of the capsule medical apparatus 10 according to the present embodiment during the image capture is described below with reference to the drawings. FIG. 4 is a detailed block diagram of the configuration of the capsule medical apparatus 10 according to the present embodiment.

As shown in FIG. 4, the capsule medical apparatus 10 includes a first circuit 110 and a second circuit 120, the first circuit 110 including the control unit 11, the signal processing unit 12, the sending unit 13, the storage unit 14, and the imaging unit 15, and the second circuit 120 including the illuminating unit 16. The second circuit 120 further includes an electric storage unit 121 that stores therein a charge and a booster circuit 122 that boosts the electric power to be supplied to the illuminating unit 16.

Between the first circuit 110 and the second circuit 120, there is provided a switch SW18 that connects/disconnects between the power supply unit 17/the first circuit 110 and the second circuit 120. A control voltage generated by a timing control unit 11*a* of the control unit 11 is applied to a control terminal of the switch SW18. Upon receiving, for example, a high-level control voltage Vcont, the switch SW18 is switched off and thus the first circuit 110 is disconnected from the second circuit 120. Upon receiving, for example, a low-level control voltage Vcont, the switch SW18 is switched on and thus the first circuit 110 is connected to the second circuit 120. The power supply unit 17 is, for example, a primary battery such as a button battery.

The electric storage unit 121 of the second circuit 120 is, for example, a capacitor or a secondly battery. When the switch SW18 is switched on, i.e., the power supply unit 17 is connected to the second circuit 120, a charge is stored in the electric storage unit 121 in accordance with the electric power from the power supply unit 17. On the other hand, when the switch SW18 is switched off, i.e., the power supply unit 17 is disconnected from the second circuit 120, the electric storage unit 121 supplies the stored charge to the illuminating unit 16 via the booster circuit 122. Thus, the illuminating unit 16 illuminates. The electric storage unit 121 has a capacity large enough to store therein the electric power that is necessary for the illuminating unit 16 to illuminate at least one time.

The booster circuit 122 boosts the electric power received from the electric storage unit 121 to a level almost the same as the level of a driving voltage for the illuminating unit 16, and the booster circuit 122 is, for example, a charge pomp circuit and a DC-DC converter. The booster circuit 122 receives the control voltage Vcont from the timing control unit 11*a*. During a period when, for example, receiving the certain control voltage Vcont in response to which the switch SW18 is switched off, the booster circuit 122 boosts the electric power received from the electric storage unit 121 and supplies the boosted electric power to the illuminating unit 16. The booster circuit 122 can be configured in such a manner that the electric storage unit 121/the power supply unit 17 and the illuminating unit 16 are electrically disconnected from each other during a period when, for example, receiving the certain control voltage Vcont in response to which the switch SW18 is switched on so that the electric power cannot flow from the power supply unit 17 or the electric storage unit 121 to the illuminating unit 16. It is allowable to set a control signal for the switch SW18 and a control signal for the booster circuit 122, respectively, and controls the switch SW18 and the booster circuit 122 individually. In this case, the booster circuit 122 can operate after the switch SW18 is switched off.

Figure 5:
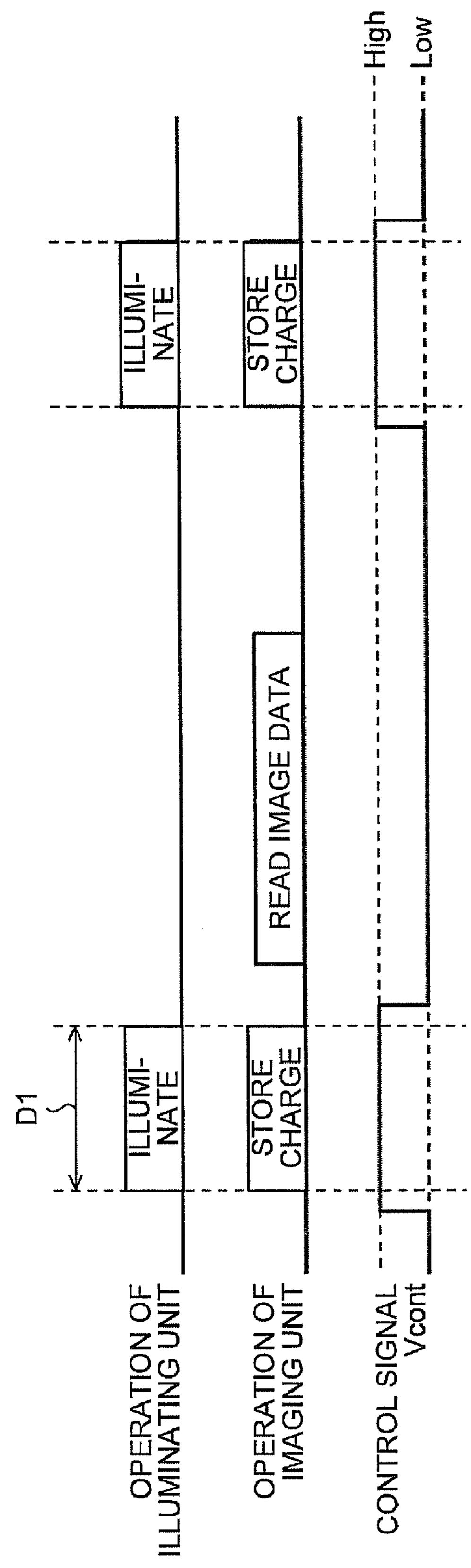
FIG. 5 is a timing chart that illustrates the relations among a control voltage, the operation of an imaging unit, and the operation of an illuminating unit according to the first embodiment of the present invention.

The control voltage Vcont that is used to control both the switch SW18 and the booster circuit 122 is described with reference to the drawings. FIG. 5 is a timing chart that illustrates the relations among the control voltage Vcont, the operation of the imaging unit 15, and the operation of the illuminating unit 16 according to the present embodiment.

As shown in FIG. 5, the timing control unit 11*a* outputs the high-level control voltage Vcont at least during a period D1 when the illuminating unit 16 illuminates and the charge is stored in the light-receiving element 15*a* of the imaging unit 15 (see FIG. 3). Thus, the switch SW18 is switched off and the power supply unit 17 is set disconnected from the second circuit 120. As a result, the electric power stored in the electric storage unit 121 is supplied to the illuminating unit 16 via the booster circuit 122 and the illuminating unit 16 illuminates. The power supply unit 17 is disconnected from the second circuit 120 during this period; therefore, it is possible to suppress a steep decrease in the power-supply voltage that may be caused by the driving of the illuminating unit 16. As a result, stable operation of the capsule medical apparatus 10 (especially, the first circuit 110) is achieved when the illuminating unit 16 is in operation.

On the other hand, when the illuminating unit 16 is not in operation, for example, when the imaging unit 15 reads the image data from the light-receiving element 15*a*, the timing control unit 11*a* outputs the low-level control voltage Vcont. Thus, the switch SW18 is switched on, the first circuit 110 is set connected to the second circuit 120, and the electric power from the power supply unit 17 is stored in the electric storage unit 121. The first circuit 110 operates by the electric power received from the power supply unit 17, regardless whether the illuminating unit 16 operates or not.

With the above configuration and operation, in the present embodiment, the power supply unit 17 (first power supplying unit) that supplies the electric power to the imaging unit 15 is electrically disconnected, by operation of the switch SW18, from the electric storage unit 121 (second power supplying unit) that supplies the electric power to the illuminating unit 16 at least during the illuminating period (D1) of the lighting unit; therefore, it is possible to prevent the voltage of the power supply unit 17 from being unstable during the illuminating period.

Figure 6:
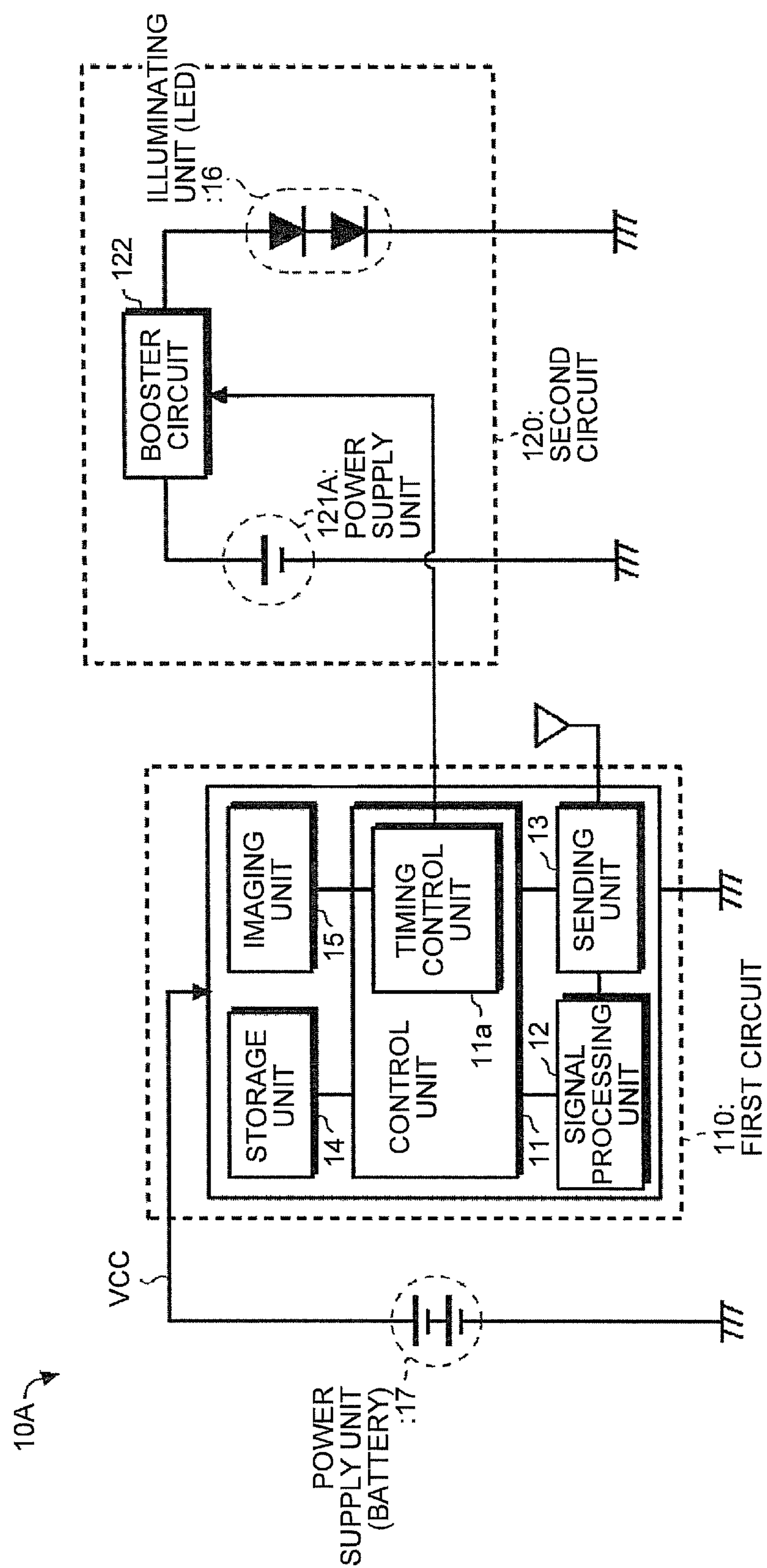
FIG. 6 is a block diagram of another embodiment that is compared for reference with the capsule medical apparatus according to the first embodiment of the present invention.

An example of the capsule medical apparatus 10 according to the present embodiment is illustrated in FIG. 6. A capsule medical apparatus 10A shown in FIG. 6 has almost the same configuration as that of the capsule medical apparatus 10 shown in FIG. 4 but both the first circuit 110 and a second circuit 120A have dedicated power supply units, i.e., the power supply unit 17 and a power supply unit 121A, respectively. As is shown, it is possible to have separated power sources for the illuminating unit 16 and the other circuits (11, 12, 13, 14, and 15).

Second Embodiment

A medical system according to a second embodiment of the present invention is described in detail below with reference to the drawings. In the following description, the parts the same as those of the medical system 1 according to the above first embodiment are denoted with the same reference number and the detailed description is omitted.

Figure 7:
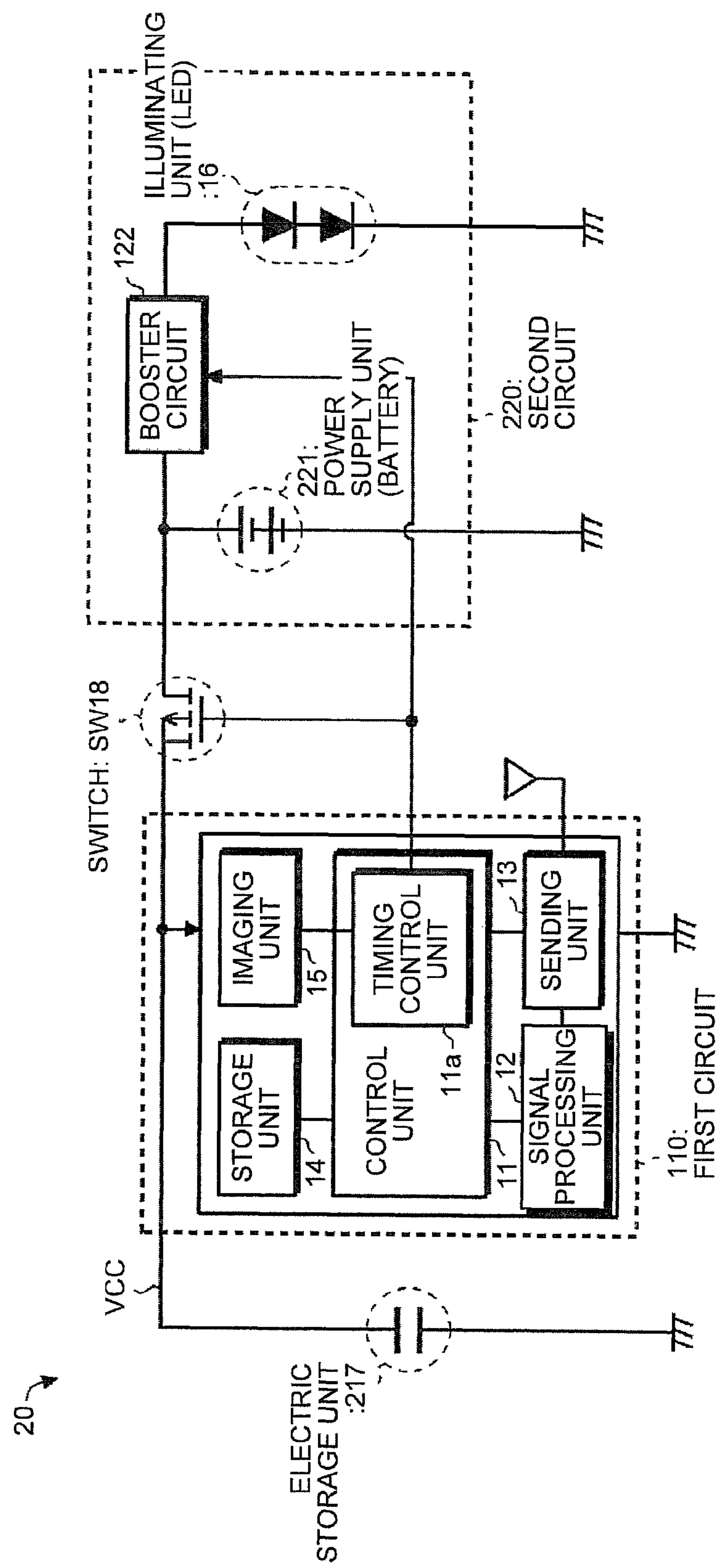
FIG. 7 is a block diagram of the configuration of a capsule medical apparatus according to the second embodiment of the present invention.

The medical system according to the present embodiment has almost the same configuration as that of the medical system 1 according to the above first embodiment. In the present embodiment, another apparatus shown in FIG. 7 is used instead of the capsule medical apparatus 10 shown in FIG. 4 according to the first embodiment. FIG. 7 is a block diagram of the configuration of a capsule medical apparatus 20 according to the present embodiment.

As shown in FIG. 7, the capsule medical apparatus 20 according to the present embodiment includes an electric storage unit 217 and a second circuit 220 instead of the power supply unit 17 and the second circuit 120 of the capsule medical apparatus 10 shown in FIG. 4. The second circuit 220 includes a power supply unit 221 instead of the electric storage unit 121 of the second circuit 120. The other components are the same as those of the capsule medical apparatus 10 shown in FIG. 4.

The electric storage unit 217 is, for example, a capacitor or a secondary battery that has a capacity large enough to store therein the electric power necessary for the first circuit 110 to operate during a period when the booster circuit 122 drives the illuminating unit 16. When the switch SW18 is switched on, the electric power from the power supply unit 221 of the second circuit 220 is stored in the electric storage unit 217. On the other hand, when the switch SW18 is switched off, the electric storage unit 217 supplies the stored charge to the first circuit 110.

Figure 8:
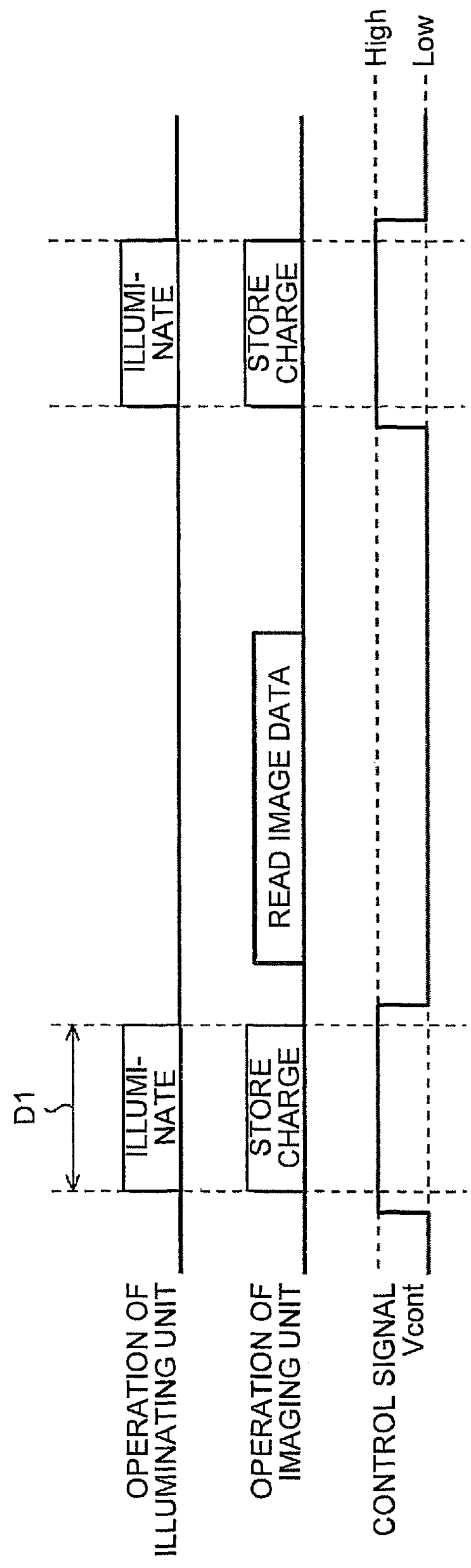
FIG. 8 is a timing chart that illustrates the relations among the control voltage, the operation of the imaging unit, and the operation of the illuminating unit according to the second embodiment of the present invention.

The control voltage Vcont according to the present embodiment is described in detail with reference to the drawings. FIG. 8 is a timing chart that illustrates the relations among the control voltage Vcont, the operation of the imaging unit 15, and the operation of the illuminating unit 16 according to the present embodiment.

As shown in FIG. 8, the timing control unit 11*a* outputs the high-level control voltage Vcont at least during the period D1 when the illuminating unit 16 illuminates and the charge is stored in the light-receiving element 15*a* of the imaging unit 15 (see FIG. 3). Thus, the switch SW18 is switched off and the first circuit 110 is set disconnected from the power supply unit 221. As a result, the electric power stored in the electric storage unit 217 is supplied to the first circuit 110. The illuminating unit 16 receives the electric power from the power supply unit 221 via the booster circuit 122. Thus, at least during the period when the illuminating unit 16 is in operation, the first circuit 110 operates by the electric power received from the electric storage unit 217 and the illuminating unit 16 operates by the electric power received from the power supply unit 221. The first circuit 110 is disconnected from the power supply unit 221 during this period; therefore, it is possible to suppress a steep decrease in the voltage of the electric storage unit 217 that may be caused by the driving of the illuminating unit 16. As a result, stable operation of the capsule medical apparatus 20 (especially, the first circuit 110) is achieved when the illuminating unit 16 is in operation.

On the other hand, when the illuminating unit 16 is not in operation, for example, when the imaging unit 15 reads the image data from the light-receiving element 15*a*, the timing control unit 11*a* outputs the low-level control voltage Vcont. Thus, the switch SW18 is switched on and the electric power is supplied from the power supply unit 221 to both the first circuit 110 and the electric storage unit 217. It means that during the period when the illuminating unit 16 is not in operation, the first circuit 110 operates by the electric power received from the electric storage unit 217 and the electric storage unit 217 stores therein the electric power received from the power supply unit 221. It is allowable to set a control signal for the switch SW18 and another control signal for the booster circuit 122, respectively, and controls the switch SW18 and the booster circuit 122 individually. In this case, the booster circuit 122 can operate after the switch SW18 is switched off.

With the above configuration and operation, in the present embodiment, the electric storage unit 217 (first power supplying unit) that supplies the electric power to the imaging unit 15 is electrically disconnected, by operation of the switch SW18, from the power supply unit 221 (second power supplying unit) that supplies the electric power to the illuminating unit 16 at least during the illuminating period (D1) of the lighting unit; therefore, it is possible to prevent the voltage of the electric storage unit 217 from being unstable during the illuminating period.

Third Embodiment

A medical system according to a third embodiment of the present invention is described in detail below with reference to the drawings. In the following description, the parts the same as those of any of the medical systems according to the first and the second embodiments are denoted with the same reference number and the detailed description is omitted.

Figure 9:
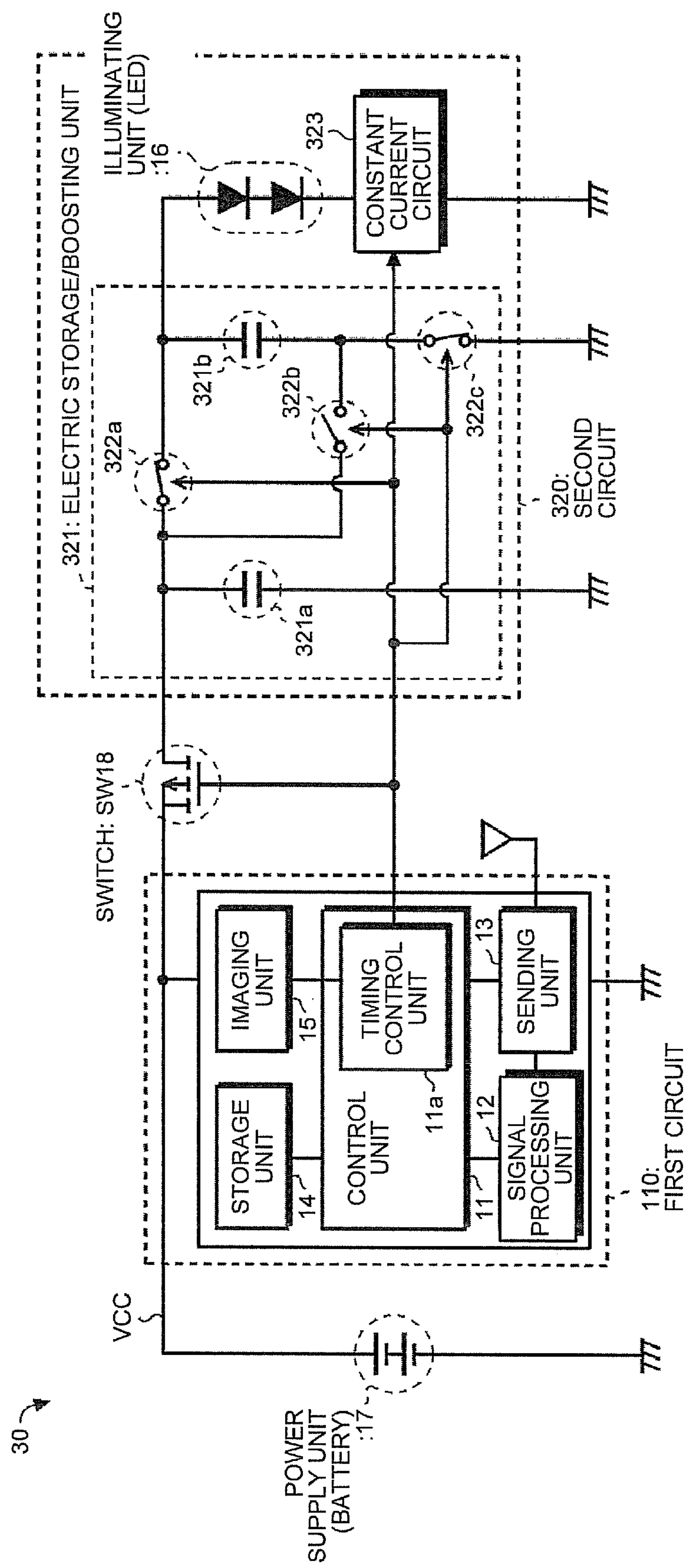
FIG. 9 is a block diagram of the configuration of a capsule medical apparatus according to the third embodiment of the present invention.
Figure 10A:
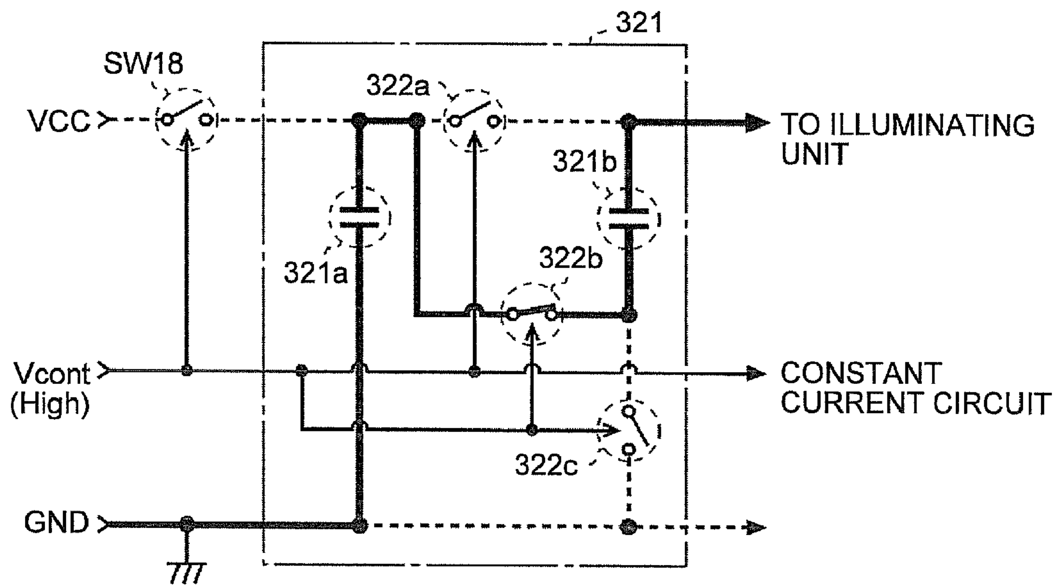
FIG. 10A is a circuit diagram that illustrates the connection state of an electric storage/booting unit according to the third embodiment of the present invention when the control voltage is at a low level.
Figure 10B:
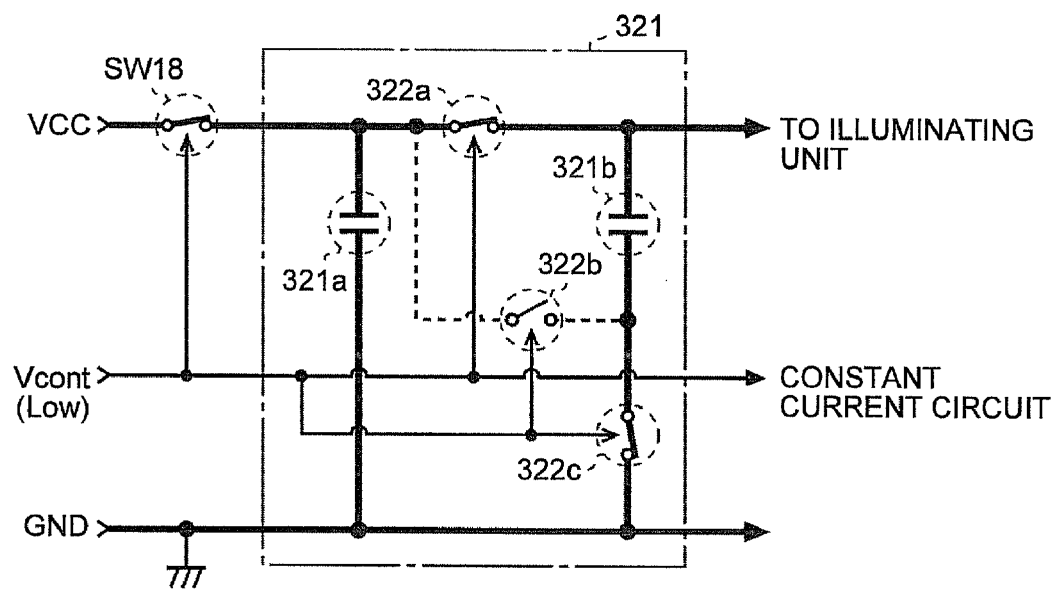
FIG. 10B is a circuit diagram that illustrates the connection state of the electric storage/booting unit according to the third embodiment of the present invention when the control voltage is at a high level.

The medical system according to the present embodiment has almost the same configuration as that of the medical system 1 according to the above first embodiment. In the present embodiment, another apparatus shown in FIG. 9 is used instead of the capsule medical apparatus 10 shown in FIG. 4 according to the first embodiment. FIG. 9 is a block diagram of the configuration of a capsule medical apparatus 30 according to the present embodiment. FIG. 10A is a circuit diagram that illustrates the connection state of an electric storage/booting unit 321 according to the present embodiment when the control voltage Vcont is at the low level; FIG. 10B is a circuit diagram that illustrates the connection state of the electric storage/booting unit 321 according to the present embodiment when the control voltage Vcont is at the high level.

As shown in FIG. 9, the capsule medical apparatus 30 according to the present embodiment includes a second circuit 320 instead of the second circuit 120 of the capsule medical apparatus 10 shown in FIG. 4. Moreover, the second circuit 320 includes the electric storage/booting unit 321 instead of the electric storage unit 121 and the booster circuit 122 and further includes a constant current circuit 323 that controls the current to be input to the illuminating unit 16. The other components are the same as those of the capsule medical apparatus 10 shown in FIG. 4.

As shown in FIG. 9, the electric storage/booting unit 321 includes two capacitors 321*a* and 321*b* between a power wire VCC to which a power-supply voltage Vcc is applied and a grounding wire GND at a grounding potential $V_{GND}$; and a first switch 322*a*, a second switch 322*b*, and a third switch 322*c* that switch, in accordance with the control voltage Vcont received from the timing control unit 11*a*, the connection relation between the capacitors 321*a* and 321*b* to either the parallel connection to the series connection. Each of the capacitors 321*a* and 321*b* can be a secondary battery.

When, for example, the first, second, and third switches 322*a* to 322*c* receive the low-level control voltage Vcont, i.e., when the switch SW18 is switched off and the power supply unit 17 is disconnected from the second circuit 320, the connection relation is switched as shown in the bold line of FIG. 10A so that the two capacitors 321*a* and 321*b* are arranged in series between the grounding wire GND and the illuminating unit 16. Therefore, in this situation, the boosted electric power is applied to the illuminating unit 16 in accordance with the charge stored in the two capacitors 321*a* and 321*b*. Thus, the illuminating unit 16 illuminates. The broken lines shown in FIG. 10A indicate disconnected and inoperable wires.

On the other hand, when, for example, the first, second, and third switches 322*a* to 322*c* receive the high-level control voltage Vcont, i.e., when the switch SW18 (see FIG. 4) is switched on and the power supply unit 17 is connected to the second circuit 320, the connection relation of the electric storage/booting unit 321 is switched as shown in the bold line of FIG. 10B so that the two capacitors 321*a* and 321*b* are arranged in parallel between the power wire VCC and the grounding wire GND. Therefore, in this situation, the charge is stored in the two capacitors 321*a* and 321*b*. The broken lines shown in FIG. 10B indicate disconnected and inoperable wires.

Figure 11:
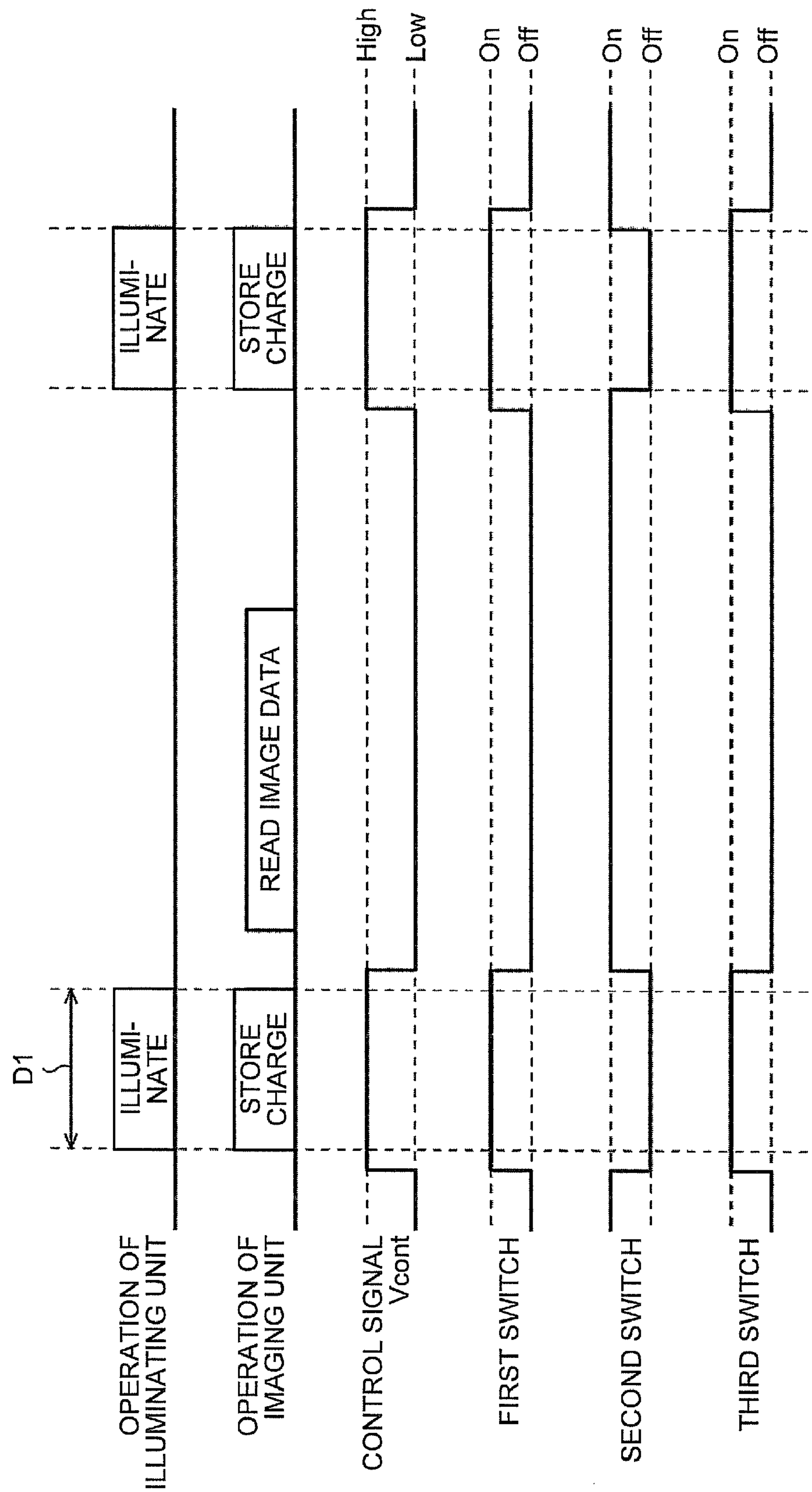
FIG. 11 is a timing chart that illustrates the relations among the control voltage, the operation of the imaging unit, the operation of the illuminating unit, and the operation of a first, second, and third switch according to the third embodiment of the present invention.

The control voltage Vcont according to the present embodiment is described in detail below with reference to the drawings. FIG. 11 is a timing chart that illustrates the relations among the control voltage Vcont, the operation of the imaging unit 15, the operation of the illuminating unit 16, and the operations of the first, second, and third switches 322*a* to 322*c* according to the present embodiment.

As shown in FIG. 11, the timing control unit 11*a* outputs the high-level control voltage Vcont at least during the period D1 when the illuminating unit 16 illuminates and the charge is stored in the light-receiving element 15*a* of the imaging unit 15 (see FIG. 3). Thus, the switch SW18 is switched off, and the power wire VCC between the first circuit 110 and the second circuit 320 is in disconnection. In this situation, the first switch 322*a* and the third switch 322*c* are switched on and the second switch 322*b* is switched off. Thus, as shown in FIG. 10A, the two capacitors 321*a* and 321*b* are connected to each other in series between the grounding wire GND and the illuminating unit 16. Therefore, the illuminating unit 16 receives the boosted electric power from the two capacitors 321*a* and 321*b* that are arranged in series. In this situation, the power wire VCC between the first circuit 110 and the second circuit 320 is in disconnection; therefore, it is possible to suppress a steep decrease in the power-supply voltage Vcc that may be caused by the driving of the illuminating unit 16. As a result, stable operation of the capsule medical apparatus 30 (especially, the first circuit 110) is achieved when the illuminating unit 16 is in operation.

On the other hand, when the illuminating unit 16 is not in operation as shown in FIG. 11, for example, when the imaging unit 15 reads the image data from the light-receiving element 15*a*, the timing control unit 11*a* outputs the low-level control voltage Vcont. Thus, the switch SW18 is switched on, the power wire VCC between the first circuit 110 and the second circuit 320 is in connection, and the electric power is supplied from the power supply unit 17 to both the first circuit 110 and the second circuit 320. In this situation, the first switch 322*a* and the third switch 322*c* are switched off and the second switch is switched on. Thus, as shown in FIG. 10B, the two capacitors 321*a* and 321*b* are connected to each other in parallel between the grounding wire GND and the power wire VCC, and the electric power from the power supply unit 17 is stored in each of the capacitors 321*a* and 321*b*. During the period when the illuminating unit 16 is not in operation, the first circuit 110 operates by the electric power received from the power supply unit 17 and the electric storage/booting unit 321 of the second circuit 320 stores therein the electric power received from the power supply unit 221.

The constant current circuit 323 is used to adjust, for example, the current in the illuminating unit 16 constant. When, for example, the high-level control voltage Vcont is received from the timing control unit 11*a*, the constant current circuit 323 adjusts the current so that the illuminating unit 16 receives the constant current.

With the above configuration and operation, in the present embodiment, the power supply unit 17 (first power supplying unit) that supplies the electric power to the imaging unit 15 is electrically disconnected, by operation of the switch SW18, from the electric storage/booting unit 321 (second power supplying unit) that supplies the electric power to the illuminating unit 16 at least during the illuminating period (D1) of the lighting unit; therefore, it is possible to prevent the power supply voltage VCC from being unstable during the illuminating period.

According to the above embodiments, the first power supplying unit that supplies the electric power to the imaging unit is electrically disconnected from the second power supplying unit that supplies the electric power to the illuminating unit at least during the period when the illuminating unit illuminates (the illuminating period); therefore, it is possible to provide a body-insertable apparatus that can prevent the power-supply voltage from being unstable during the illuminating period.

The above and other features, advantages and technical and industrial significance of this invention will be better understood by reading the following detailed description of presently preferred embodiments of the invention, when considered in connection with the accompanying drawings.

What is claimed is:

1. A body-insertable apparatus comprising:

an illuminating unit that illuminates the inside of a subject's body;

an imaging unit that takes an image of the inside of the subject's body;

a first power supplying unit that supplies electric power to the imaging unit;

a second power supplying unit that supplies electric power to the illuminating unit; and a switch that either connects the first power supplying unit to the second power supplying unit or disconnects the first power supplying unit from the second power supplying unit, wherein the switch electrically separates the first power supplying unit from the second power supplying unit during at least an illuminating period of the illuminating unit, the electric power for the illuminating unit is supplied from only the second power supplying unit during the illuminating period of the illuminating unit, the second power supplying unit includes a plurality of charge storage units and a plurality of switches that switch a connection state between the charge storage units to either a series connection or a parallel connection, the plurality of switches switch the connection state between the charge storage units to the series connection during at least the illuminating period of the illuminating unit, and the plurality of switches switch the connection state between the charge storage units to the parallel connection during at least a part of the period other than during the illuminating period of the illuminating unit, and the charge storage units store therein the electric power received from the first power supplying unit during at least the part of the period other than during the illuminating period of the illuminating unit and supplies the stored electric power to the illuminating unit during at least the illuminating period of the illuminating unit.

2. The body-insertable apparatus according to claim 1, wherein the second power supplying unit stores therein the electric power received from the first power supplying unit and supplies the stored electric power to the illuminating unit.

3. The body-insertable apparatus according to claim 1, wherein the first power supplying unit stores therein the electric power received from the second power supplying unit and supplies the stored electric power to the imaging unit.

4. The body-insertable apparatus according to claim 1, further comprising a boosting unit that boosts the electric power received from the second power supplying unit and supplies the boosted electric power to the illuminating unit.

5. The body-insertable apparatus according to claim 1, wherein the first power supplying unit is a primary battery, and the second power supplying unit is a secondary battery or a capacitor that stores therein the electric power received from the first power supplying unit.

6. The body-insertable apparatus according to claim 1, wherein the second power supplying unit is a primary battery, and the first power supplying unit is a secondary battery or a capacitor that stores therein the electric power received from the second power supplying unit.

* * * * *